(12) United States Patent
Paul et al.

(10) Patent No.: US 10,954,342 B2
(45) Date of Patent: Mar. 23, 2021

(54) AMINO-ORGANOPOLYSILOXANES AND PREPARATION METHOD THEREFOR

(71) Applicant: Wacker Chemie AG, Munich (DE)

(72) Inventors: Amit Kumar Paul, Kolkata (IN);
Sougata Bhattacharya, Kolkata (IN);
Sunanda Biswas, Nadia (IN)

(73) Assignee: WACKER CHEMIE AG, Munich (DE)

( * ) Notice: Subject to any disclaimer, the term of this patent is extended or adjusted under 35 U.S.C. 154(b) by 134 days.

(21) Appl. No.: 16/095,019

(22) PCT Filed: Apr. 19, 2016

(86) PCT No.: PCT/EP2016/058667
§ 371 (c)(1),
(2) Date: Oct. 19, 2018

(87) PCT Pub. No.: WO2017/182061
PCT Pub. Date: Oct. 26, 2017

(65) Prior Publication Data
US 2019/0119450 A1 Apr. 25, 2019

(51) Int. Cl.
| | |
|---|---|
| *C08L 83/08* | (2006.01) |
| *C08G 77/26* | (2006.01) |
| *C08G 77/46* | (2006.01) |
| *D06M 15/00* | (2006.01) |
| *A61Q 5/12* | (2006.01) |
| *C08L 83/12* | (2006.01) |
| *A61K 8/898* | (2006.01) |
| *D06M 15/643* | (2006.01) |
| *C08G 77/12* | (2006.01) |
| *C08G 77/14* | (2006.01) |

(52) U.S. Cl.
CPC .............. *C08G 77/26* (2013.01); *A61K 8/898* (2013.01); *A61Q 5/12* (2013.01); *C08G 77/46* (2013.01); *C08L 83/08* (2013.01); *C08L 83/12* (2013.01); *D06M 15/00* (2013.01); *D06M 15/6436* (2013.01); *C08G 77/12* (2013.01); *C08G 77/14* (2013.01); *D06M 2200/50* (2013.01)

(58) Field of Classification Search
None
See application file for complete search history.

(56) References Cited

U.S. PATENT DOCUMENTS

| | | | |
|---|---|---|---|
| 5,807,956 A | 9/1998 | Czech | |
| 6,114,299 A | 9/2000 | Hunter | |
| 6,307,000 B1 | 10/2001 | Wong | |
| 6,326,061 B1 | 12/2001 | Lautenschlager | |
| 2004/0048996 A1 | 3/2004 | Lange | |
| 2004/0186308 A1 | 9/2004 | Koch | |
| 2008/0261473 A1 | 10/2008 | Will | |
| 2010/0243944 A1 | 9/2010 | Herzig | |
| 2013/0121948 A1* | 5/2013 | Dussaud | C08L 83/08 424/70.122 |
| 2013/0123529 A1* | 5/2013 | Lu | C08G 77/46 556/423 |

FOREIGN PATENT DOCUMENTS

| | | | |
|---|---|---|---|
| CN | 101418518 A | 4/2009 | |
| CN | 102617863 A | 8/2012 | |
| CN | 103214679 A | 7/2013 | |
| DE | 19524816 A1 * | 1/1997 | ............. C08G 77/42 |
| JP | 2010133062 A2 | 6/2010 | |
| WO | WO9732917 A1 | 9/1997 | |
| WO | WO9913151 A1 | 3/1999 | |
| WO | WO0123394 A1 | 4/2001 | |
| WO | WO07145867 A1 | 12/2007 | |
| WO | WO08127519 A1 | 10/2008 | |
| WO | WO09085298 A2 | 7/2009 | |
| WO | WO13074912 A1 | 5/2013 | |

OTHER PUBLICATIONS

Qian et al. "Synthesis and Properties of Silicone Polyetheramine Block Copolymer Surfactant" Fibers and Polymers 2014, 15, 195-199. (Year: 2014).*
Gelest data sheet for hydride-terminated polydimethylsiloxanes, 1 page, 2016. (Year: 2016).*
Huntsman brochure for Jeffamine Polyetheramines, 11 pages, 2016. (Year: 2016).*
Huang et al. "Synthesis and properties of terminated amino polyether silicone surfactant" Textile Auxiliaries, 31, 2014, 5 pages. (Year: 2014).*

* cited by examiner

*Primary Examiner* — Robert S Loewe
(74) *Attorney, Agent, or Firm* — Brooks Kushman P.C.

(57) ABSTRACT

Hydrophilic amino-organopolysiloxane softener compositions are prepared by reacting a hydrogen siloxane, a mixture of an allyl epoxy and optionally an allyl polyether in presence of catalyst comprising platinum and then reacting the epoxy functional siloxane product with a polyetheramine to obtain an amino-organopolysiloxane. The hydrophilic amino-organopolysiloxane softener composition is preferably used in the form of an emulsion. Textile fabrics treated by the inventive composition have strong hydrophilic performance and enhanced smoothness and feel.

19 Claims, No Drawings

AMINO-ORGANOPOLYSILOXANES AND PREPARATION METHOD THEREFOR

CROSS REFERENCE TO RELATED APPLICATIONS

This application is the U.S. National Phase of PCT Appln. No. PCT/EP2016/058667 filed Apr. 19, 2016, the disclosures of which are incorporated in their entirety by reference herein.

BACKGROUND OF THE INVENTION

1. Field of the Invention

The present invention is related to a hydrophilic silicone polymer for improving and balancing the feel and hydrophilicity of natural or artificial fibers. The present invention also relate to the process of preparation of the hydrophilic silicone polymer and emulsion.

2. Description of the Related Art

Synthetically produced fibers (such as polyester, polyamide or polyolefin fibers or their blends) are often so hydrophobic that no water or no perspiration can be absorbed. Even natural fibers treated ("finished") with aminosilicones loose hydrophilicity after finishing, since the silicone forms a hydrophobic film on the textile surface. It is also observed that fabrics of natural fibers also become very hydrophobic due to changes in OH group orientation in cellulose after mercerization. These all ultimately develop uncomfortable properties in textile finishing. This very unpleasant property for the wearer of such textiles can be completely eliminated by treatment of the textile fibers or of the textiles with textile softeners. The textiles are rendered hydrophilic thereby. Perspiration can then be absorbed, and the comfort level is simultaneously improved significantly. Furthermore the textiles treated with hydrophilic softener acquire a pleasant soft handle.

Previous attempts to improve the hydrophilicity of textiles were done either by grafting hydrophilic moieties to the textile or fabric or by coating a hydrophilic coating on the textile or fabric. These attempts either affect the main fabric polymer or will have less retention properties if coated.

Thus it has been attempted to prepare hydrophilic softeners consisting mainly of acylated amino silicones, but these have very poor hand feel. Also, standard amino silicone containing effluent is not allowed in the recycling of waste water for purification by reverse osmosis in textile processing plants and needs to be replaced. This is one of the major reasons for a shift in the textile market from standard amino silicones to hydrophilic softener derivatives. There are different approaches that are taken in the prior art.

JP 2010-133062 describes a fiber treating agent composition having a high wrinkle-reducing performance, giving a good touch, and exhibiting a high lingering scent property.

U.S. Pat. No. 6,307,000 B1 describes a multifunctional nonionic or partially nonionic siloxane copolymer for modification of synthetic materials and methods for modifying synthetic materials with the siloxane copolymer. Synthetic materials modified with the siloxane copolymer, and fabrics made from the modified synthetic materials, have improved hydrophilicity, thermal regulative properties, and simultaneously improved softening effects and hand.

US 2004/0186308 A1 describes amido-functional aminopolydiorganosiloxanes, especially for a finishing agent, which exhibit a high yellowing resistance in addition to improved soft feel properties, and which can be applied on high-shear application systems without difficulty.

U.S. 2008/0261473 A1 relates to a polysiloxane with at least one epoxy radical and a polyether radical as well as at least one quaternary nitrogen atom as a textile auxiliary which contains at least one polysiloxane. The invention is directed to appropriately modifying the polysiloxanes further to such an extent that the compatibility with anions, in particular polyanions and anionic auxiliaries, is improved.

WO 2007/145867 A1 describes a method of treating textiles with a silicone block copolymer containing polyether-amide units. Textiles treated with the silicone block copolymer have a feel or hand comparable to conventional hydrophobic silicones, but do not negatively impact the hydrophilicity of the textile.

U.S. Pat. No. 6,114,299 A describes aqueous textile treating compositions containing both nitrogen-functional organopolysiloxanes and oligomeric polyisobutylene polymers which are stated to be as effective as conventional textile treating compositions containing only nitrogen-functional organopolysiloxanes, and which have improved resistance to yellowing, improved wash fastness, and are more cost effective. Stable concentrates containing amino-functional organopolysiloxane, polyisobutylene, and a blend-stabilizing surfactant may be used to form aqueous emulsion and microemulsion fabric softener compositions.

WO/9913151 A1 relates to a method for treating textiles, using a composition containing at least one silane or organosiloxane which has at least one monovalent SiC-bonded radical with primary, secondary and/or tertiary amino groups, and at least one Si—O—C-bonded (iso) oxyalkyl radical.

WO/0123394 relates to novel organosilicon compounds with amido groups, of a general formula (I), wherein R are monovalent carbohydrate radicals, R1 are hydrogen atom, an alkyl radical, or an alkoxyalkyl radical, Y are radicals of the formula $-(R^4-NA-)_zR^4-NR^3A$, R3 are hydrogen or an alkyl radical, $R^4$ is a divalent hydrocarbon radical, A is a radical $R^3$ or a radical F of formula $-C(=O)R^2$, $R^2$ are monovalent saturated or unsaturated hydrocarbon radicals with at least 16 carbon atoms, preferably of a fatty acid, z is 0 or a whole number from 1 to 10, a is 0, 1, 2 or 3, c is 0, 2 or 3 and d is 0, 1, 2, or 3, on the condition that the sum of a, c and d in the units of formula (I) is less than or equal to 3 and at least one radical Y with at least one radical F is contained per molecule.

WO 2009/085298 A2 describes an asymmetric organomodified disiloxane surfactant having the formula: MM' wherein M comprises branched hydrocarbon substituents and M' comprises a cationic, anionic or zwitterionic substituent and a polyether substituent that may be combined as one moiety, wherein the disiloxane surfactant has an enhanced resistance to hydrolysis between a pH of about 3 to about 12.

US 2010/243944 A1 describes a polysiloxane containing both epoxy groups and quaternary ammonium groups bonded to the polysiloxane through ring-opened epoxy groups to provide a soft hand and wash fastness to fibrous substrates.

US 2004/0048996A1 describes polyammonium-polysiloxane compounds, their manufacture, and their use as wash-resistant hydrophilic softeners, whereby the polyammonium-polysiloxane compounds bestow a soft touch typical of silicones upon the textiles.

WO 2008/127519 A1 describes silicone polyether copolymers having the average formula $E-B-[AB]_n-E$ where E is an organofunctional end blocking group, B is a diorganopolysiloxane. A is a divalent organic group comprising at least one polyether group, and n is 1. The silicone polyether copolymers having an amine functional end blocking group are useful in the treatment of textiles and fibers.

US 2004/0048996 A1 relates to polyammonium-polysiloxane compounds, a method for the production and use thereof, in which polyammonium-polysiloxane compounds in which siloxane and alkylene oxide substructures are joined with each other through ammonium structures, are useful as wash resistant softeners. These polysiloxane compounds have in chain bivalent or trivalent bridging quaternary ammonium groups. However, such repeating structures do not give the desired hydrophilicity and hand feel balance, and due to the secondary or tertiary amine group in the molecule, they do not give proper anchorage and hence wash fastness.

CN 103214679 A describes the preparation of aminopolyether modified polysiloxane deforming agents and preparation thereof, where in a first step (1) hydrogen silicones of the formula

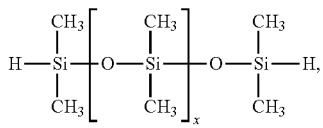

are reacted with allyl glycidyl ether
wherein the molar ratio of Si—H to C=C is from 1:1.2-1.4 and an epoxy-modified silicone is obtained
and in a second step (2), the epoxy-modified silicone obtained in the first step (1) is reacted with polyether amine of the formula

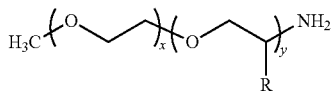

wherein, x=1, 6 or 19, y=3, 9 or 29 and R=H or $CH_3$, wherein, the molar ratio of the amino group to the epoxy group is 1-1.2:1.

Such aminopolyether modified polysiloxanes do not render proper balance of hydrophilicity and feel to the natural fibers and the polyether amines used do not render proper anchorage due to the presence of an alkyl group at its terminus.

WO 2013/074912 A1 discloses an A-B-A type copolymer where the amine groups used are secondary amine or a tertiary amine and thus the anchorage with the textile deteriorates due to the presence of the alkyl moieties.

U.S. Pat. No. 5,807,956 A and WO 97/32917 describe non-hydrolyzable, block, $(AB)_n$ A-type copolymers comprising alternating units of polysiloxane and amino-polyalkyleneoxide and provide a method for the preparation of these copolymers, where, the amine groups used are secondary amine or tertiary amine and thus the anchorage with the textile may deteriorate due to the presence of the alkyl moieties. Again, the $(AB)_nA$ type of block copolymer is hydrophobic in nature and does not render required hydrophilicity.

Though there are many prior art attempts, achieving a balance between the hand feel and hydrophilicity is a desirable property which is in need of improvement.

It is thus an object of the invention to present amino-organopolysiloxanes that are suitable as hyrophilic softeners for textiles. The textiles are rendered hydrophilic thereby, and furthermore the textiles acquire a pleasant soft handle with improved water absorption properties.

It is thus a basic objective of this invention to provide a hydrophilic textile softener composition comprising a hydrophilic amino-organopolysiloxane softener that imparts a balanced and improved hand feel and hydrophilicity in the textile, and which is cost effective as well.

SUMMARY OF THE INVENTION

The present invention provides an amino-organopolysiloxane of the formula

wherein,
$R^*$ is R or $R^1$,
R is the same or different and is a monovalent $C_1$ to $C_{20}$ hydrocarbon radical,
$R^1$ is the same or different and is a $C_1$ to $C_6$ alkoxy radical or a hydroxyl radical,
Y is the same or different and is a polyetheramine group D of the formula

is a polyether group G of the formula

$R^2$ is the same or different and is a $C_1$ to $C_{10}$ alkylene radical,
$R^3$ is the same or different and is a $C_1$ to $C_{10}$ alkylene radical,
A is —$CH_2CH_2$ $(CH_2)_w$O—$R^5$CH(OH)—$CH_2$—,
$R^5$ is the same or different and is a linear $C_1$ to $C_6$ alkylene radical or a cyclic $C_3$ to $C_8$ alkylene radical,
w is an integer from 1 to 20,
Z and $Z^1$ are the same or different and are a hydrogen atom or a $C_1$ to $C_6$ alkyl group, preferably a hydrogen atom,
f is an integer from 1 to 100, preferably from 1 to 70,
g is an integer from 1 to 100, preferably from 1 to 70,
m is an integer from 1 to 500,
with the provision that on average from 20 to 100 mol %, preferably from 80 to 100 mol %, of radicals Y are polyetheramine groups D and from 0 to 80 mol %, preferably from 0 to 20 mol %, of radicals Y are polyether groups G.

The invention also provides a method for the preparation of compounds of the formula (I).

DETAILED DESCRIPTION OF THE PREFERRED EMBODIMENTS

The process for preparing the amino-organopolysiloxane comprises:
(i) reacting in a first step
a hydrogen siloxane of the formula

wherein R and R* are each as defined earlier,
u is an integer from 1 to 500,
with
an olefinic unsaturated epoxy compound of the formula

wherein $R^5$ and w are each as defined earlier, and
optionally an olefinic unsaturated polyether of the formula

wherein $R^9$ is $C_1$ to $C_4$ alkylene radical,
in the presence of a catalyst comprising platinum or its compounds or complexes
to form an epoxy functional siloxane;
with the proviso that the olefinic unsaturated epoxy compound is used in an amount of from 0.2 to 1 mol, preferably from 0.8 to 1 mol, of the olefinic unsaturated radical (C=C) in the epoxy compound per 1 mol Si-bonded hydrogen in the hydrogen siloxane and the olefinic unsaturated polyether is used in an amount of from 0 to 0.8 mol, preferably from 0 to 0.2 mol, of the olefinic unsaturated radical (C=C) in the polyether per 1 mol Si— bonded hydrogen in the hydrogen siloxane,
(ii) reacting in a second step
the resulting epoxy functional siloxane obtained from the first step with a polyetheramine of the formula $$NZ_2R^3(OR^2)_fNZ^1_2 \qquad (VII)$$

wherein $R^2$, $R^3$, Z, $Z^1$, and f are each as defined earlier, with the proviso that the polyetheramine is used in an amount of more than 1 mol of amino group in the polyetheramine per 1 mol epoxy group in the epoxy functional siloxane, to obtain an amino-organopolysiloxane.

According to the basic aspects of the present invention there is provided an amino-organopolysiloxane of the formula $$R^*_2YSiO(R_2SiO)_mSiYR^*_2 \qquad (I),$$

wherein,
$R^*$ is R or $R^1$,
R is the same or different and is a monovalent $C_1$ to $C_{20}$ hydrocarbon radical,
$R^1$ is the same or different and is a $C_1$ to $C_6$ alkoxy radical or a hydroxyl radical,
Y is the same or different and is a polyetheramine group D of the formula $$\text{-A-NZ—}R^3\text{—}(OR^2)_f\text{—}NZ^1_2 \qquad (II) \text{ or}$$

is a polyether group G of the formula $$—R^3(OR^2)_gOH \qquad (III)$$

$R^2$ is the same or different and is a $C_1$ to $C_{10}$ alkylene radical,
$R^3$ is the same or different and is a $C_1$ to $C_{10}$ alkylene radical,
A is —$CH_2CH_2$ $(CH_2)_w$O—$R^5CH(OH)$—$CH_2$—,
$R^5$ is the same or different and is a linear $C_1$ to $C_6$ alkylene radical or a cyclic $C_3$ to $C_8$ alkylene radical,
w is an integer from 1 to 20,
Z and $Z^1$ are the same or different and are a hydrogen atom or a $C_1$ to $C_6$ alkyl group, preferably a hydrogen atom,
f is an integer from 1 to 100, preferably from 1 to 70,
g is an integer from 1 to 100, preferably from 1 to 70,
m is an integer from 1 to 500,
with the proviso that on average from 20 to 100 mol %, preferably from 80 to 100 mol %, of radicals Y are polyetheramine groups D and from 0 to 80 mol %, preferably from 0 to 20 mol %, of radicals Y are polyether groups G.

In the amino-organopolysiloxane of formula (I), more preferably from 80 to 90 mol % of radicals Y are polyetheramine groups D and more preferably from 10 to 20 mol % of radicals Y are polyether groups G.

The viscosity of the amino-organopolysiloxane is preferably from 100 to 15,000 mPa·s at 25° C. The amine value of the amino-organopolysiloxane is preferably from 2 to 60 mg of KOH per gram of polymer.

In one of the embodiments, $R^2$ and $R^3$ are same or different and are preferably a $C_2$ or $C_3$ alkylene radical. Most preferably, $R^2$ and $R^3$ are $C_3$ alkylene radicals. A non-limiting example is an iso-propylene radical.

The invention also provides a process for preparing the amino-organopolysiloxane comprising:
(i) reacting in a first step
a hydrogen siloxane of the formula $$HR^*_2SiO(R_2SiO)_uSiR^*_2H \qquad (IV),$$

wherein R and $R^*$ are each as defined earlier,
u is an integer from 1 to 500,
with
an olefinic unsaturated epoxy compound of the formula $$CH_2=CH—(CH_2)_w—O—R^5—CH(O)CH_2 \qquad (V),$$

wherein $R^5$ and w are each as defined earlier, and optionally an olefinic unsaturated polyether of the formula $$CH_2=CH—R^9—(OR^2)_gOH \qquad (VI),$$

wherein $R^9$ is $C_1$ to $C_4$ alkylene radical,
in the presence of a catalyst comprising platinum or its compounds or complexes, to form an epoxy functional siloxane; with the proviso that the olefinic unsaturated epoxy compound is used in an amount of from 0.2 to 1 mol, preferably from 0.8 to 1 mol, of the olefinic unsaturated radical (C=C) in the epoxy compound per 1 mol Si-bonded hydrogen in the hydrogen siloxane and the olefinic unsaturated polyether is used in an amount of from 0 to 0.8 mol, preferably from 0 to 0.2 mol, of the olefinic unsaturated radical (C=C) in the polyether per 1 mol Si— bonded hydrogen in the hydrogen siloxane,
(ii) reacting in a second step
the resulting epoxy functional siloxane obtained from the first step with a polyetheramine of the formula $$NZ_2R^3(OR^2)_fNZ^1_2 \qquad (VII)$$

wherein $R^2$, $R^3$, Z, $Z^1$, and f are each as defined earlier,
with the proviso that the polyetheramine is used in an amount of more than 1 mol of amino group in the polyetheramine per 1 mol epoxy group in the epoxy functional siloxane, to obtain an amino-organopolysiloxane.

In the first step of the process of the present invention more preferably the olefinic unsaturated epoxy compound is used in an amount of from 0.8 to 0.9 mol of the olefinic unsaturated radical (C=C) in the epoxy compound per 1 mol Si-bonded hydrogen in the hydrogen siloxane and more preferably the olefinic unsaturated polyether is used in an amount of from 0.1 to 0.2 mol of the olefinic unsaturated radical (C=C) in the polyether per 1 mol Si— bonded hydrogen in the hydrogen siloxane. In one non-limiting embodiment, the olefinic unsaturated epoxy compound and the olefinic unsaturated polyether is reacted in the first step either simultaneously or stepwise and also either mixed together or dosed separately either at a predetermined rate or at a predetermined quantity at a predetermined interval.

A hydrogen silicone is commercially available from Wacker Chemie AG as Wacker H-polymer 55.

The invention provides an aqueous composition comprising the amino-organopolysiloxane of the present invention, wherein the composition is an aqueous emulsion.

The invention provides a process for treating organic fibers with an aqueous composition comprising an amino-organopolysiloxane of the present invention.

Preferably, the amino-organopolysiloxane of the present invention is used as a hydrophilic softener.

In one of the embodiments, the hydrophilic softener which is the amino-organopolysiloxane may be a selected from siloxanes with one end terminated with polyether and other end terminated with epoxy further reacted with polyetheramine, a siloxane with both ends terminated with epoxy (i.e. α,ω-diepoxysiloxane) and further reacted with polyetheramine, and a siloxane with both ends terminated with polyether, or its mixtures thereof. The major structures are selected from:

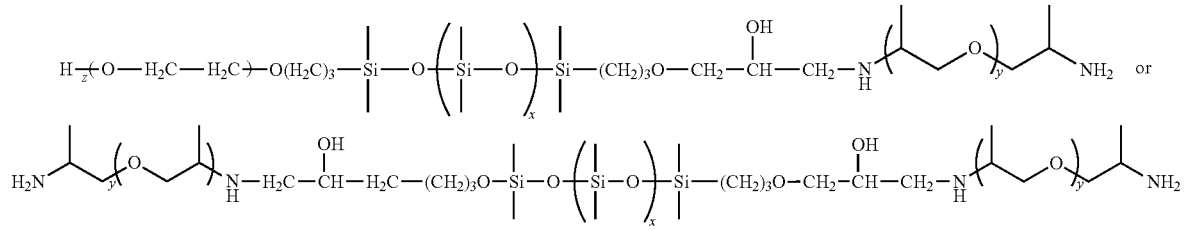

or mixtures thereof.

The invention provides a process for treating organic fibers, wherein the aqueous composition is an aqueous emulsion. Preferably, the process for treating organic fibers improves the hydrophilicity and softness of the organic fibers.

Preferably in the process, the organic fiber is a textile fabric.

In one of the embodiments, the amine value is determined by acid-base titration using a potentiometer [Make: Veego; Model: VPT-MG]. 0.6 g of sample is taken in a 500 ml beaker and toluene-butanol 1:1 mixture is added and stirred to mix the sample thoroughly and the sample solution is titrated with a 0.1 (N) HCl solution. The amine value is calculated according to the formula (56.11×V×N)/W mg KOH/g of sample,
where, V=Volume of HCl required in ml
N=Normality of HCl i.e. 0.1 N
W=Weight of the sample taken in gram.

In one aspect of the invention, the amine value of the amino-organopolysiloxane is preferably between 2 and 60 mg of KOH per gram of polymer. Most preferably, the amine value is between 20 and 60 mg of KOH per gram of polymer.

In the process of the present invention an olefinic unsaturated epoxy compound of the formula $$CH_2=CH-(CH_2)_w-O-R^5-CH(O)CH_2 \qquad (V)$$

is used, wherein $R^5$ is a linear $C_1$ to $C_6$ alkylene radical or a cyclic $C_3$ to $C_8$ alkylene radical and w is an integer from 1 to 20. The (O) group represents the bridge oxygen group linked to the two carbon atoms. The most preferable and suitable olefinic unsaturated epoxy compound includes:
$CH_2=CH-(CH_2)-O-CH_2-CH(O)CH_2$,

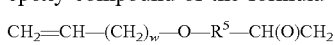

$CH_2=CR-(CH_2)_w-O-R^5-CH(O)CH_2$,
$CH_2=CR-(CH_2)_w-R^5-CH(O)CH_2$,
wherein R is a methyl radical.

The olefinically unsaturated epoxy compound is preferably allyl glycidyl ether [$CH_2=CH-(CH_2)-O-CH_2-CH(O)CH_2$] 1-allyloxy-2,3-epoxypropane, or allyl 2,3-epoxypropyl ether, available from Sigma-Aldrich. The olefinically unsaturated epoxy compound is preferably used in an amount of from 0.8 to 1 mol of the olefinic unsaturated radical (C=C) in the epoxy compound per 1 mol Si-bonded hydrogen in the hydrogen siloxane.

Olefinically unsaturated polyethers are preferably selected from polyethylene glycol allyl methyl ether $CH_2=CHCH_2(OC_2H_4)_nOH$; $CH_2=CHCH_2(OC_3H_6)_nOH$; polyalkylene glycol allyl methyl ether (EO/PO random) $CH_2=CHCH_2O(C_2H_4O)_l(C_3H_6O)_kH$, where l and k are integers from 2 to 100, preferably from 20 to 40 and more preferably from 25 to 30. A non-limiting example of a preferred olefinically unsaturated polyether is allyloxy(polyethylene oxide) (EO 29) available as Polymeg 1200AP from IGL, India. The olefinically unsaturated polyether is preferably used in an amount of from 0 to 0.2 mol of the olefinic unsaturated radical (C=C) in the polyether per 1 mol Si—bonded hydrogen in the hydrogen siloxane.

The polyetheramine or polyoxyalkylene polyamine used according to the present invention contains polyoxyalkylene, capped with diamine in alpha, omega positions of the molecule, or a mixture thereof. The carbon chain in the alkylene part in the alkylene ether may be $C_2$ to $C_6$, most preferably $C_2$ or $C_3$, or mixtures thereof. The polyoxyalkylene chain length may vary from 1 to 100, most preferably 5 to 40. The polytheramines are commercially available as Jeffamine diamines, including the D, ED, and EDR series products. Jeffamine T series products are triamines, the SD Series and ST Series products consist of secondary amine versions (from Huntsman), or 4,7-dioxadecane-1,10-diamine; 4,9-dioxadecane-1,12-diamine; 4,7,10-trioxatridecane-1,13-diamine, polyetheramine D230, polyetheramine D400, polyetheramine D2000, polyetheramine T403 from BASF, or mixture thereof. The most preferable polyetheramine, used according to the present invention is a primary polyetherdiamine which is a polyoxyalkylene capped with primary diamine in alpha, omega positions of the molecule, or mixture thereof. A most preferable non-limiting example of a polyetheramine is a polyoxypropylene capped with primary diamine in alpha, omega positions. Excess of greater than or equal to 20 mole percent of polyoxyalkylene polyamine to that of the epoxy functional siloxane is preferably used during the preparation of the copolymers, and the majority of the terminal groups of the product are expected to be amino groups.

In the second step of the process of the present invention the polyetheramine is preferably used in an amount of equal to or greater than 1.2 mols of amino groups in the polyetheramine per 1 mol epoxy group in the epoxy functional siloxane.

Preferably R is same or different and is a $C_1$ to $C_{20}$ alkyl radical. Examples of alkyl radicals R are the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals such as the n-hexyl radical, heptyl radicals such as the n-heptyl radical, octyl radicals such as the n-octyl radical and isooctyl radicals such as the 2,2,4- trimethylpentyl radical, nonyl radicals such as the n-nonyl radicals, decyl radicals such as the n-decyl radical, dodecyl radicals such as the n-dodecyl radical, and octadecyl radicals such as the n-octadecyl radical. Preferably, R is a methyl radical.

$R^1$ is a $C_1$ to $C_6$ alkoxy radical or a hydroxyl radical. Examples for $C_1$ to $C_6$ alkoxy radicals are the methoxy, ethoxy, propoxy, butoxy, pentoxy, and hexoxy radicals or their isomers or mixtures thereof.

In the process for preparing the amino-organopolysiloxane a solvent can be used.

The solvents used are generally non-reactive solvents. The preferable solvent used is 2-ethyl-1-hexanol. It is possible that the epoxy end group on the polysiloxane can undergo side reactions with the solvent, water or alcohol, to form the respective diol or ether alcohol.

The epoxycyclohexane is used to stop the back donation reaction for the allyl functional molecules during hydrosilylation reaction using platinum catalyst.

In another aspect of the invention, the viscosity of the amino-organopolysiloxane is at least 50 mPa·s at 25° C. and more preferably from 100 to 15,000 mPa·s at 25° C. Viscosity is measured by Anton Paar Rheometer; model MCR101, geometry single gap cylinder: CC 27 spindle or cone plate of 60 mm diameter and 2° and shear rate 1 s$^{-1}$. The viscosity value is taken at 60 sec. measured at shear rate=1 s$^{-1}$, temperature of 25° C. The measurement is repeated thrice. MCR Rheometer Series products work as per USP (US Pharmacopeia Convention) 912—Rotational Rheometer methods.

The catalysts for the hydrosilylation reaction in the first step preferably comprise a metal from the group of the platinum metals, or a compound or a complex from the group of the platinum metals. Examples of such catalysts are metallic and finely divided platinum, which may be present on supports, such as silicon dioxide, aluminum oxide or activated carbon, compounds or complexes of platinum, such as platinum halides, e.g. $PtCl_4$, $H_2PtCl_6 \cdot 6H_2O$, $Na_2PtCl_4 \cdot 4H_2O$, platinum-olefin complexes, platinum-alcohol complexes, platinum-alkoxide complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, such as platinum-1,3-divinyl-1,1,3,3-tetramethyl-disiloxane complexes with or without detectable inorganically bonded halogen, bis(gamma-picoline)platinum dichloride, trimethylenedipyridineplatinum dichloride, dicyclopentadieneplatinum dichloride, dimethylsulfoxide-ethyleneplatinum(II) dichloride, cyclooctadiene-platinum dichloride, norbornadiene-platinum dichloride, gamma-picoline-platinum dichloride, cyclopentadiene-platinum dichloride, and also reaction products of platinum tetrachloride with olefin and primary amine or secondary amine, or primary and secondary amine, such as the reaction product of platinum tetrachloride in solution in 1-octene with sec-butylamine, or ammonium-platinum complexes.

Preferably, the reaction is carried out between 70 to 110° C., more preferably from 80 to 100° C., in the presence of a catalyst, preferably hexachloroplatinic acid, preferably in the range of 500 to 5000 ppm by weight. The reaction is preferably carried out in absence of oxygen, i.e. under an $N_2$ atmosphere.

In the process for preparing the amino-organopolysiloxane, $R^2$ and $R^3$ are same or different and are preferably a $C_2$ or $C_3$ alkylene radical. Most preferably, $R^2$ and $R^3$ is a $C_3$ alkylene radical and a non-limiting example is an isopropylene radical.

In another embodiment of the invention, the aqueous emulsion has a surfactant or emulsifier, which is chosen from anionic, cationic or non-ionic emulsifiers, preferably cationic or non-ionic emulsifiers or mixtures thereof, and most preferably non-ionic emulsifiers or mixtures of non-ionic emulsifiers.

According to another aspect of the present invention there is provided an aqueous composition comprising the amino-organopolysiloxane of the present invention. Preferably the aqueous composition is an aqueous emulsion.

According to another aspect of the present invention there is provided a composition, preferably a concentrate composition, comprising the amino-organopolysiloxane of the present invention. Preferably, the concentrate composition comprises the amino-organopolysiloxane from 1 to 99 weight percent, more preferably from 50 to 99 weight percent, an emulsifier from 0.1 to 20 weight percent, more preferably from 5 to 20 weight percent, acetic acid or its derivatives from 0.1 to 10 weight percent, more preferably from 0.1 to 5 weight percent, and optionally a biocide, preferably as per the required permitted quantity, all based on the total weight of the composition. In another aspect of the present invention water, preferably demineralized (DM) water, is added to the concentrate composition to obtain the aqueous composition comprising the amino-organopolysiloxane.

Preferably, the aqueous composition comprises the amino-organopolysiloxane of the present invention from 5 to 99 weight percent, more preferably from 5 to 70 weight percent, most preferably from 5 to 40 weight percent, an emulsifier from 0.1 to 20 weight percent, more preferably from 0.1 to 10 weight percent, acetic acid or its derivatives from 0.1 to 10 weight percent, more preferably from 0.1 to 10 weight percent, most preferably from 0.1 to 5 weight percent, and optionally a biocide, preferably as per the required permitted quantity, and water, wherein the amounts of water is adding up to 100 weight percent.

In one of the embodiments, in the emulsion, in acidic medium, the nitrogen atom of the amine end group in the amino-organopolysiloxane group will obtain a positive valency to form $N^+$, where, $M^-$ is an anionic group, preferably an anion of a corresponding acid, such as a carboxylate anion, for example an acetate anion, to the $N^+$ can be obtained.

Particularly suitable non-ionic emulsifiers include alkyl polyglycol ethers, alkylated fatty alcohol alkyl aryl polyglycol ethers, ethylene oxide/propylene oxide (EO/PO) block polymers, fatty acids, natural substances and their derivatives, such as lecithin, lanolin, saponins, cellulose; cellulose alkyl ethers and carboxyalkylcelluloses, saturated and unsaturated alkoxylated fatty amines. Preferable non-ionic emulsifiers are alkylated fatty alcohols, a non-limiting example of alkylate fatty alcohol being a polyoxyether of lauryl alcohol ($CH_3(CH_2)_{10}CH_2OH$).

The subject process for treating, i.e. impregnating, organic fibers is useful with all organic fibers, for example in the form of filaments, yarns or as textile fabrics such as webs, mats, strands, woven, loop-formingly knitted or loop-drawingly knitted textiles, as have hitherto been treatable with organosilicon compounds. Examples of fibers, which can be treated by the process according to the invention, are fibers composed of keratin, especially wool, polyvinyl alcohol, interpolymers of vinyl acetate, cotton, rayon, hemp, natural silk, polypropylene, polyethylene, polyester, polyurethane, polyamide, cellulose, and blends of at least two such fibers. As it is clear from the preceding enumeration, the fibers can be of any natural or synthetic origin. The textiles or textile fabrics can be present in the form of fabric webs or garments or parts of garments.

In one of the other elements, hydrophilicity of the amino-organopolysiloxane composition is measured by water absorbency time in seconds of fabrics coated with the same amino-organopolysiloxane composition measured according to drop test of AATCC Test Method 79-2010. It can be used on textiles of any fiber content or construction, including woven, knit and nonwoven.

Water Retention of Terry towel—ASTM D 4772-97 (Reapproved 2004): This test method is used to test the surface water absorption of terry fabrics by water flow for bath towels, bath sheets, hand towels, kitchen towels, dishcloths, washcloths, beachwear, bathrobes and the like. This test method determines the ability of a terry fabric to rapidly absorb and retain liquid water from surfaces such as human skin, dishes, and furniture.

Vertical Wicking of Textiles—AATCC Test Method 197-2013: This test method is used to evaluate the ability of vertically aligned fabric specimens to transport liquid along and/or through them, and is applicable to woven, knitted, or nonwoven fabrics.

A handfeel test is done by the following process: first, after the padding process, the treated fabric or textile is conditioned for 6 hours at a temperature of 35° C. and Relative Humidity (RH) 60. The conditioned fabric is transferred to a temperature of 25° C. at RH 50.

Five panelists are fixed and it is made sure that they have grease free hands. The fabric is then folded two times at the same face side. The handfeel is performed by horizontally rubbing the folded fabric along the surface of the fabric and averaging the score by each panelist.

The amino-organopolysiloxane according to the present invention is also suitable to use as a conditioning agent for hair or skin, and also for use as an antifoam in anionic base detergent composition and also as a wetting agent in different industrial applications.

The details of the invention, its nature and objects are explained hereunder in greater detail in relation to the following non-limiting examples.

EXAMPLES

Preparation Examples

Example 1: (Inventive Example)

Step 1.1: Preparation of Epoxy Functional Siloxane (Siloxane with Epoxy and Allyloxy (Polyethylene Oxide) Functional Group (with Solvent)

1040 g of 2-Ethyl-1-hexanol (solvent) is loaded in a jacketed glass reactor and the temperature is set to 100° C. at process mode under $N_2$ purging. After 2 hours 1153 g (0.548 moles of Si-bonded H) of a dimethylhydrogensiloxy terminated polydimethylsiloxane (Wacker H-polymer 55) having a viscosity of 60 mPa·s at 25° C. and hydrogen content of 0.05% by weight is transferred into the 5 liter glass reactor and 2 g cyclohexene oxide are loaded in the reactor under stirring and $N_2$— purging. When the temperature has reached 100° C., 0.3 g of Pt-catalyst (2% in iso-propanol) is added to the reaction vessel. 111.6 g allyloxy(polyethylene oxide) (EO 29) (0.084 moles) and 60.4 g (0.53 moles) of allyl glycidyl ether in 200 g of 2-Ethyl-1-hexanol (solvent) dosing is started at 2 ml/min under $N_2$ purging. After complete addition of allyl compounds, the reaction is continued for 1 hour. Then add 0.2 g catalyst solution is added at 100° C. and the reaction continued for 1.5 hours. Then the reaction progress is checked by $^1$H-NMR.

If all Si—H is not consumed then again 0.2 g catalyst solution is added and the reaction continued under the same conditions. Thereafter NMR analysis is carried out to measure the quantity of unreacted Si—H (<1%). If reaction is not complete then it should be continued. When the Si—H concentration is below 1%, the reactor is cooled down, and the epoxy fluid product is collected.

The primary compound formed is of the structure:

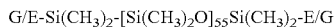

wherein
E=—$(CH_2)_3$—O—$CH_2$—CH(O)$CH_2$
G=—$CH_2CH_2CH_2$—O$(CH_2CH_2O)_{29}$H and
85 mol % of the end groups are epoxy groups E and
15 mol % of the end groups are polyether groups G.

This structure is confirmed by $^1$H-NMR Shift (ppm) $CH_2$=CH—$CH_2$—R 5.84 ppm which is absent in the compound formed and new $^1$H-NMR Shift (ppm) of SiCH$_2$ at 0.52 ppm.

Step 1.2: Preparation of Amino Fluid 1 (the Mole Ratio is in an Amount of More than 1 Mol (20 Mole % Excess) of the Polyetheramine Per 1 Mol of Epoxy Group in the Epoxy Functional Siloxane)

With 800 g of Epoxy Fluid solution from Step 1.1 (having 0.166 moles of epoxy group), 398.4 g Jeffamine D-2000 (0.1992 moles of Jeffamine D 2000), a polyether amine of the formula $NH_2[CH(CH_3)CH_2O]_xCH_2CH(CH_3)NH_2$ with x is about 33.1 available under the trade name Jeffamine® D-2000 from Huntsman, and 150 g 2-Ethyl-1-hexanol are loaded into a glass reactor and temperature set to 170° C. under $N_2$ purging. The mixture appears hazy white. Reaction is continued for 7 h after the temperature reaches 150° C. The $^1$H-NMR is used to monitor reaction advancement. Distillation begins when reaction is completed at 150° C. under vacuum (760 mmHg) for 2 h. That product is the cooled down. A clear yellow fluid 1 is obtained at 50° C. with a viscosity of 1570 mPa·s at 50° C. with amine value of 25.5 mg KOH/g.

To elucidate the chemical structure $^1$H NMR, $^{13}$C-jmode-APT, 2D-HSQC & 2D-HMBC was performed in CDCl$_3$ solvent in Bruker 400 MHz Ascend NMR Spectroscopy.

A product with the following structure is obtained:

wherein
D=E—J=—$(CH_2)_3$—O—$CH_2$—CH(OH)$CH_2$—NH—[CH$(CH_3)CH_2O]_x$—$CH_2CH(CH_3)$—$NH_2$ with x=33.1
G=—$CH_2CH_2CH_2$—O$(CH_2CH_2O)_{29}$H and
85 mol % of the end groups are polyether amine groups D and
15 mol % of the end groups are polyether groups G.

Example 2 (Inventive Example)

Step 2.1: Preparation of Epoxy Functional Siloxane (Siloxane with Epoxy and Allyloxy (Polyethelene Oxide) Functional Group (without Solvent)

2320 g of a dimethylhydrogensiloxy terminated polydimethylsiloxane (Wacker H-polymer 55) having a viscosity of 60 mPa·s at 25° C. and hydrogen content of 0.05% by weight is loaded in reaction vessel and heated to 100° C. at process temperature mode under $N_2$ (1-2 ml/min). Reaction is completed under process temperature mode. When the temperature reaches 100° C., 1.8 g epoxycyclohexane and 0.25 ml Pt-catalyst is added to the reaction vessel. Then, 226 g allyloxy(polyethelene oxide) (EO 29) and 121.6 g of allyl glycidyl ether is dosed in at the rate of 2 ml/min, through a temperature controllable feeder unit. After complete addition the mixture turns slightly hazy. After 2 h of stirring at 100° C., 0.15 g Pt-catalyst is added and the reaction continued for an hour. Si—H content is determined by $^1$H-NMR spectra and reaction is continued till the mixture is free from allyl glycidyl ether and allyloxy(polyethelene oxide) (EO 29). The reaction is continued at same condition till the mixture becomes clear. When the reaction mixture is clear, $^1$H-NMR is used to determine the Si—H content. If unreacted allyl is present the reaction is continued until all allyl is consumed. Allyl mixture is added if all Si—H is not consumed during the reaction (Si—H is determined by $^1$H-NMR and allyl glycidyl ether is added accordingly). The reaction is continued at 110° C. for 2 hours. The reaction mixture is cooled to below 50° C. and the clear colorless to light yellow epoxy fluid is removed from the reactor.

The primary compound formed is of the structure:

wherein

E=—(CH$_2$)$_3$-O—CH$_2$—CH(O)CH$_2$
G=—CH$_2$CH$_2$CH$_2$-O(CH$_2$CH$_2$O)$_{29}$H and
85 mol % of the end groups are epoxy groups E and
15 mol % of the end groups are polyether groups G.

This structure is confirmed by $^1$H-NMR Shift (ppm) CH$_2$=CH—CH$_2$—R ppm which is absent in the compound formed and new $^1$H-NMR Shift (ppm) of SiCH$_2$.

Step 2.2: Preparation of Amino Fluid 2 (the Mole Ratio is in an Amount of More than 1 Mol (20 Mole % Excess) of the Polyetheramine Per 1 Mol of Epoxy Group in the Epoxy Functional Siloxane)

With 800 g of Epoxy Fluid solution from Step 2.1 (having 0.166 moles of epoxy group), 398.4 g Jeffamine D-2000 (0.1992 moles of Jeffamine D 2000), a polyether amine of the formula NH$_2$[CH(CH$_3$)CH$_2$O]$_x$CH$_2$CH(CH$_3$)NH$_2$ with x is about 33.1 available under the trade name Jeffamine® D-2000 from Huntsman, and 150 g 2-Ethyl-1-hexanol are loaded into a glass reactor and the temperature set to 170° C. under N$_2$ purging. The mixture appears hazy white. Reaction is continued for 7 h after the temperature reaches 150° C. $^1$H-NMR is used to monitor reaction advancement. Distillation begins when the reaction is completed at 150° C. under vacuum (760 mmHg) for 2 h. After that, the product is cooled down, to yield a clear yellow fluid 2 obtained at 50° C. with a viscosity of 1950 mPa·s at 50° C. with amine value of 25.8 mg KOH/g.

A product with the following structure is obtained:

wherein

D=E-J=—(CH$_2$)$_3$—O—CH$_2$CH(OH)CH$_2$—NH—[CH(CH$_3$)CH$_2$O]$_x$—CH$_2$CH(CH$_3$)—NH$_2$ with x=33.1
G=—CH$_2$CH$_2$CH$_2$—O(CH$_2$CH$_2$O)$_{29}$H and
85 mol % of the end groups are polyether amine groups D and
15 mol % of the end groups are polyether groups G.

Similarly, to elucidate the chemical structure $^1$H NMR, $^{13}$C-jmode-APT, 2D-HSQC & 2D-HMBC has been performed in CDCl$_3$ solvent in Bruker 400 MHz Ascend NMR Spectroscopy.

Example 3 (Inventive Example)

Step 3.1: Preparation of Epoxy Fluid

Before starting all the reactions in this reactor, all surfaces inside the reactor including pipe lines, condenser, reflux lines etc. must be cleaned and free from all chemicals which are poison for platinum catalyst for addition reactions. 3500 grams of dimethylhydrogensiloxy terminated polydimethylsiloxane (Wacker H-polymer 55) having a viscosity of 60 mPa·s at 25° C. and hydrogen content of 0.05% by weight are transferred into a 5 liter glass reactor. H-polymer is loaded and stirred under N$_2$ at process temperature (Tp) 60° C. for 40 min. 268 g allyl glycidyl ether is added and the process temperature (Tp) is set to 80° C. under N$_2$. When Tp is 80° C. then 0.2 ml Pt-catalyst is added and an immediate exotherm up to 89° C. (Tp) is observed. After 1.5 h again 44 g allyl glycidyl ether is added and 0.2 ml catalyst is added at Tp=80° C. is continued; an exotherm observed up to Tp=82-83° C. The reaction is continued for another 1 h. Then, the Tp is set to 100° C., and the reaction is continued at Tp=100° C. under N$_2$ for 1 h. After 1 h, 0.4 ml catalyst is added at Tp=100° C., no exotherm is found. The reaction is continued for 1 h at the same condition and then IR is used to monitor for unreacted Si—H. Reaction completion was concluded by FTIR (PerkinElmer Spectrum 100) by measuring the absorbance of residual Si—H at 2148.59 cm$^{-1}$. The Si—H intensity was found to be nearly nil, and distillation began at Tp=110° C. under 760 mmHg vacuum for 2 h. Then the product was cooled down. All materials should be free from moisture (<1000 ppm) and base. Final product should be free from Si—H, or have an Si—H content as low as possible. Appearance: clear colorless to light yellow; Viscosity: 60 to 80 mPa·s at 25° C.; Si—H content (by $^1$H-NMR) 37 ppm.

The compound formed is of the structure:

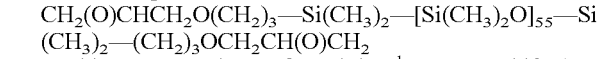

This structure is confirmed by $^1$H-NMR Shift (ppm) CH$_2$=CH—CH$_2$—R 5.84 ppm which is absent in the compound formed and new 1H-NMR Shift (ppm) of SiCH$_2$ at 0.52 ppm.

Step 3.2: Preparation of Amino Fluid 3 (the Mole Ratio is in an Amount of More than 1 Mol of the Amino Group in the Polyetheramine Per 1 Mol of Epoxy Group in the Epoxy Functional Siloxane) (20 Mole % Excess of Polyetheramine with Respect to Epoxy Functional Group in Epoxy Fluid)

1000 g Epoxy fluid from step 2.1 (having 0.45 moles of epoxy group), 216 g Jeffamine® D 400 (0.54 moles of Jeffamine D 400), a polyether amine of the formula NH$_2$[CH(CH$_3$)CH$_2$O]$_x$CH$_2$CH(CH$_3$)NH$_2$ with x of about 6.1, available under the trade name Jeffamine® D-400 from Huntsman, and 5.4 g propylene glycol are loaded and the temperature set to 150° C. under N$_2$. The mixture is hazy white. The reaction is continued for 7 h after the temperature reaches 150° C., under N$_2$. The mixture is observed to see if the mixture is clear. If the mixture is found to be clear without solvent, then the product is cooled down to form fluid 2.

Appearance: clear light yellow oil; Viscosity 560 mPa·s at a temperature of 25° C.; Amine value 45.2 mg KOH/g; Wt. loss 5.31% at 200° C./15 min/0.5 g.

The chemical structure of the product is:
NH$_2$—CH(CH$_3$)CH$_2$—[OCH$_2$CH(CH$_3$)]$_x$—NH—CH$_2$CH(OH)CH$_2$O—(CH$_2$)$_3$—Si(CH$_3$)$_2$—O—[Si(CH$_3$)$_2$O]$_{55}$Si(CH$_3$)$_2$—(CH$_2$)$_3$OCH$_2$CH(OH)CH$_2$—NH—[CH(CH$_3$)CH$_2$O]$_x$—CH$_2$CH(CH$_3$)—NH$_2$
wherein, x is about 6.1.

Example 4 (Comparison Example): The Mole Ratio is in an Amount of More than 1 Mol of the Polyether Monoamine Per 1 Mol of Epoxy Group in the Epoxy Functional Siloxane Step 4.2: Preparation of Amino Fluid 4

600 g Epoxy fluid from step 3.1 (having 0.27 moles of epoxy group), 272 g of Jeffamine M1000 (having 0,272 moles of Jeffamine M1000), a polyether monoamine of the formula $CH_3[OCH_2CH_2]_{19}[OCH_2CH(CH_3)]_3NH_2$ available under the trade name Jeffamine® M-1000 from Huntsman, and 400 g propylene glycol are loaded and temperature set to 150° C. under $N_2$. The mixture is hazy white. Reaction is continued for 6 h after the temperature reaches 150° C./$N_2$. The clarity of the mixture is checked with a small amount of mixture after removal of solvent. If the mixture is found clear without solvent, then distillation begins at 150° C. under 760 mmHg vacuum for 1.5 h. After that, the product is cooled down to form fluid 4.

Appearance: Clear red oil; Viscosity: 11,200 mPa·s at a temperature of 25° C.; Amine value: 22.7 mgKOH/g; Wt. loss: 1.63% at 200° C./15 min/0.5 g.

Example 5 (Comparison Example): Preparation of $(AB)_nA$ Copolymer According to Example 1 of U.S. Pat. No. 5,807,956

Step 5.2: Preparation of Amino Fluid 5 (Having 0.54 Moles of Jeffamine ED 2003 Per 1 Mole of Epoxy Fluid)

Before starting all the reactions in this reactor, all surfaces inside the reactor including pipe lines, condenser, reflux lines etc. must be cleaned and free from all chemicals which are poison for platinum catalyst for addition reaction. The reactor is charged with 245 g of JEFFAMINE® ED 2003 (having 0.122 moles of Jeffamine ED 2003), a polyether amine of the formula $NH_2[CH(CH_3)CH_2O]_z[CH_2CH_2O]_y[CH(CH_3)CH_2O]_xCH_2CH(CH_3)NH_2$ with y about 39 and (x+z) about 6, i.e. PO group=6 and EO group=39, available under the trade name Jeffamine® ED 2003 from Huntsman, and a sufficient amount of 2-propanol to make a 50% solution of the final copolymer is placed in the reactor, equipped with a stirrer, addition funnel, reflux condenser and thermometer. The temperature of the reaction mixture was adjusted to 80° C. and 1000 g of the Epoxy fluid from step 3.1 (having 0.2256 moles of α,ω-diepoxysiloxane having terminal epoxy groups) was added from an addition funnel in three portions, allowing 1-2 hours between additions. The reaction advancement is monitored by checking by $^1$H-NMR. If the mixture is found to be clear without solvent, then distillation begins at 150° C. under 760 mmHg vacuum for 1.5 h. After that, the product is cooled down to form fluid 5.

Appearance: brown fluid; Viscosity: 16,000 mPa·s at a temperature of 25° C.

$^1$H and $^{29}$Si NMR analysis of fluid 5 reveals average molecular weight of 7665 g/mole respectively from $^1$H- and $^{29}$Si-NMR analysis. The ratio of primary and secondary amine is about 1:7 calculated taking the peak ratio from adjacent protons of primary and secondary amine, hence it can be said that amine containing part is a $(AB)_nA$ type compound having $-(AB)_n-$ units which contains about 81% of the total molecules.

$-(AB)_n-$ Structure:
$A = -NH-[CH(CH_3)CH_2O]_z[CH_2CH_2O]_y[CH(CH_3)CH_2O]_xCH_2CH(CH_3)-NH-$ with y about 39 and (x+z) about 6
$B = -CH_2CH(OH)CH_2O(CH_2)_3-Si(CH_3)_2-O-[Si(CH_3)_2O]_{55}-Si(CH_3)_2-(CH_2)_3OCH_2CH(OH)CH_2-$
and n≥2.

Application Tests

Step A: Concentrate Preparation (Inventive Example 1)

| Sl. no. | Raw Material | Company | Quantity in wt % |
|---|---|---|---|
| 1 | Example 1, fluid 1 | | 91 |
| 2 | Laureth-4 | Croda | 7 |
| 3 | Acetic Acid | | 1.9 |
| 4 | Methylisothiazolinone | Neolone 950/Rohm & Haas | 0.1 |
| Total | | | 100.0 |

Process: Put 1 to 4 in a container and homogenize them (by rotor stator type homogenizer at 3000 rpm) for 5 min.

Step B: Emulsion Preparation Using Concentrate of Step A (Inventive Example 1)

To the prepared concentrate in Step A, DM water is added stepwise and homogenized for 10 minutes to form a stable emulsion B of pH 5. Emulsion particle size is 45 nm, which is measured by using a ZetaSizer device from Malvern.

Process: All above components are put in a container and stirred by a turbine stirrer at 200 rpm for 2 hours.

Step C: Emulsion Preparation (Inventive Example 2)

The same recipe is followed as in Step A and B for emulsion preparation, but using example 2 fluid 2 to obtain a stable emulsion C. The particle size of the emulsion is 63 nm.

Step D: Emulsion Preparation (Inventive Example 3)

The same recipe is followed as in Step A and B but using example 3 fluid 3 to obtain a stable emulsion D. The particle size of the emulsion is 65 nm.

Step E: Emulsion Preparation (Comparison Example 4)

The same recipe is followed as in Step A and B but using Example 4 fluid 4, to obtain a stable emulsion E. The particle size of the emulsion is 60 nm.

Step F: Emulsion Preparation (Comparison Example 5)

The same recipe is followed as in Step A and B but using Example 5 fluid 5, to obtain a stable emulsion F. The particle size of the emulsion is 60 nm.

Step G: Padding of Different Fabrics by B, C, D E and F Emulsions

Padding is done by using a high speed laboratory padding mangle machine made by R.B. Electronic & Engineering Pvt. Ltd, Mumbai, India, with a maximum speed of 70 mpm. The current conditions are: speed for current treatment is 50 mpm, pressure is 5 kg/cm$^2$ and in a bath having 10 grams per liter (gpl) concentration and pH 5.5 maintained by acetic acid.

TABLE 1

| | Fabric Liquid pick-up (in percent weight of the weight of fabric) | | |
|---|---|---|---|
| Fabric | Knit 100% Cotton Green | Towel 100% Cotton white | Knit 100% Polyester yellow |
| Liquor pick-up | 65% | 68% | 63% |
| Drying in stenter | 120 sec; 140° C. | 5 min; 140° C., then Tumble dried for 10 minutes | 90 sec; 170° C. |

It is a usual phenomenon that the Knit 100% polyester after treating with hydrophilic softener and during drying in stenter (LABTEC, Model D3, No 601, make—New Wave Lab Equipment Co. Ltd, Taiwan) loses its hydrophilicity and becomes hydrophobic. Whereas, for the current invention even after drying in stenter, the Knit 100% polyester fabric property of hydrophilicity does not change and remains hydrophilic.

Step H: Hydrophilicity Test

Hydrophilicity Test 1: Hydrophilicity Comparison: Hydrophilicity by Drop Test—AATCC Test Method 79-2010

The test method is for the determination of the water absorbency of yarns, fabrics and garments. It can be used on textiles of any fiber content or construction, including woven, knit and nonwoven.

TABLE 2

Cotton single jersey knit-dried at 140° C. for 60 seconds

| Product | Absorption time in sec (Less the absorption time, better the hydrophilicity) |
|---|---|
| Emulsion B | 1.0 |
| Emulsion C | 1.0 |
| Emulsion D | 2.5 |
| Emulsion E (Comparative) | 3 |
| Emulsion F (Comparative) | 3.5 |
| Blank | 1 |

TABLE 3

Polyester single jersey knit-dried at 170° C. for 40 seconds

| Product | Absorption time in sec (Less the absorption time, better the hydrophilicity) |
|---|---|
| Emulsion B | 1 |
| Emulsion C | 1 |
| Emulsion D | 3 |
| Emulsion E (Comparative) | 5 |
| Emulsion F (Comparative) | 30 |
| Blank | 10 |

Hydrophilicity Test 2: Water Retention of Terry Towel—ASTM D 4772-97 (Reapproved 2004):

This test method is used to test the surface water absorption of terry fabrics by water flow for bath towels, bath sheets, hand towels, kitchen towels, dishcloths, washcloths, beachwear, bathrobes, and the like. This test method determines the ability of a terry fabric to rapidly absorb and retain liquid water from surfaces such as human skin, dishes, and furniture.

TABLE 4

400 GSM cotton terry towel-dried at 140° C. for 5 minutes and tumble dried for 10 minutes

| Product | Water retention in % (higher the value, better the absorbency) |
|---|---|
| Emulsion B | 72 |
| Emulsion C | 75 |

TABLE 4-continued

400 GSM cotton terry towel-dried at 140° C. for 5 minutes and tumble dried for 10 minutes

| Product | Water retention in % (higher the value, better the absorbency) |
|---|---|
| Emulsion D | 69 |
| Emulsion E (Comparative) | 50 |
| Emulsion F (Comparative) | 47 |
| Blank | 70 |

Hydrophilicity Test 3: Vertical Wicking of Textiles—AATCC Test Method 197-2013

This test method is used to evaluate the ability of vertically aligned fabric specimens to transport liquid along and/or through them, and is applicable to woven, knitted, or nonwoven fabrics.

TABLE 5

Cotton Knit-dried at 140° C. for 60 seconds

| Product | Wicking height after 1 min in cm (Higher the value, better the hydrophilicity) |
|---|---|
| Emulsion B | 4.5 |
| Emulsion C | 4.5 |
| Emulsion D | 4 |
| Emulsion E (Comparative) | 2.5 |
| Emulsion F (Comparative) | 2 |
| Blank | 4.5 |

TABLE 6

Polyester Knit-dried at 170° C. for 40 seconds

| Product | Wicking height after 1 min in cm (Higher the value, better the hydrophilicity) |
|---|---|
| Emulsion B | 3.5 |
| Emulsion C | 3.6 |
| Emulsion D | 3.0 |
| Emulsion E (Comparative) | 1.5 |
| Emulsion F (Comparative) | 1.0 |
| Blank | 0.5 |

Step I: Handfeel Evaluation by Panel Test

Evaluation was done by 5 panelists to judge the softness. Then the final hand feel ranking was taken as an average of 5 individual rankings.

TABLE 7

Handfeel evaluation

| Product | Handfeel ranking | | |
|---|---|---|---|
| | Cotton knit | Polyester knit | Towel |
| Emulsion B | 9 | 9 | 10 |
| Emulsion C | 10 | 10 | 8 |
| Emulsion D | 10 | 10 | 8 |
| Emulsion E (Comparative) | 8 | 8 | 7 |
| Emulsion F (Comparative) | 8 | 8 | 7 |
| Untreated | 0 | 0 | 0 |

Handfeel ranking=10 means best hand feel
Handfeel ranking=0 means poor hand feel So, from the above examples the emulsion compositions prepared by Example 1, 2 and 3 fluid (inventive Examples) the ABA type of molecule is formed which is obtained as the mole ratio of polyetheramine which is used in an amount of more than or equal to 1.2 mol amino group in the polyetheramine per 1 mol epoxy group in the epoxy functional siloxane. Such emulsion compositions prepared (Emulsion B, C and D) by Example 1, 2 and 3 fluid shows an improved balance in hydrophilicity and handfeel properties compared with Example 4 fluid (Comparison Example) and Example 5 fluid (Comparison Example), obtained emulsions E and F, and blank product. The current inventive amino-organopolysiloxane of formula (I) imparts a balance property of hydrophilicity and handfeel and thus is a desirable textile softener. There is another marked advantage that the wash fastness using the fluid 1, 2 and 3 than by treating with other comparative fluids.

This result and experiments are non-limiting and is not restricted to this certain composition and process. They may vary and minor variations in composition and process may give similar result.

The invention claimed is:

1. An amino-organopolysiloxane of the formula $$R^*_2YSiO(R_2SiO)_mSiYR^*_2 \qquad (I),$$

wherein, $R^*$ is R or $R^1$,

R is the same or different and is a monovalent $C_1$ to $C_{20}$ hydrocarbon radical, $R^1$ is the same or different and is a $C_1$ to $C_6$ alkoxy radical or a hydroxyl radical, Y is the same or different and is a polyetheramine group D of the formula $$-A-NZ-R^3-(OR^2)_f-NZ^1_2 \qquad (II) \text{ or}$$

is a polyether group G of the formula $$-R^3(OR^2)_gOH \qquad (III)$$

$R^2$ is the same or different and is a $C_1$ to $C_{10}$ alkylene radical, $R^3$ is the same or different and is a $C_1$ to $C_{10}$ alkylene radical, A is $-CH_2CH_2(CH_2)_wO-R^5CH(OH)-CH_2-$, $R^5$ is the same or different and is a linear $C_1$ to $C_6$ alkylene radical or a cyclic $C_3$ to $C_8$ alkylene radical, w is an integer from 1 to 20, Z and $Z^1$ are the same or different and are hydrogen or a $C_1$ to $C_6$ alkyl group, f is an integer from 1 to 100, g is an integer from 1 to 100, and m is an integer from 1 to 500, with the provision that on average from 20 to less than 100 mol %, of radicals Y are polyetheramine groups D and from greater than 0 to 80 mol % of radicals Y are polyether groups G.

2. The amino-organopolysiloxanes of claim 1, wherein Z and $Z^1$ are hydrogen, f is an integer from 1 to 70, g is an integer from 1 to 70.

3. The amino-organopolysiloxane of claim 1, wherein $R^2$ and $R^3$ are the same or different and are $C_2$ or $C_3$ alkylene radicals.

4. The amino-organopolysiloxane of claim 1, wherein the viscosity of the amino-organopolysiloxane is from 100 to 15,000 mPa·s at 25° C.

5. The an amino-organopolysiloxane of claim 1, wherein the amine value of the amino-organopolysiloxane is from 2 to 60 mg of KOH per gram of polymer.

6. A process for preparing an amino-organopolysiloxane of claim 1, comprising:

(i) reacting in a first step
a hydrogen siloxane of the formula $$HR^*_2SiO(R_2SiO)_uSiR^*_2H \qquad (IV),$$

wherein u is an integer from 1 to 500, with an olefinic unsaturated epoxy compound of the formula $$CH_2=CH-(CH_2)_w-O-R^5-CH(O)CH_2 \qquad (V),$$

and an olefinic unsaturated polyether of the formula $$CH_2=CH-R^9-(OR^2)_gOH \qquad (VI),$$

wherein $R^9$ is $C_1$ to $C_4$ alkylene radical, in the presence of a catalyst comprising platinum or its compounds or complexes, to form an epoxy functional siloxane;

with the proviso that the olefinic unsaturated epoxy compound is used in an amount of from 0.2 to 1 mol, of the olefinic unsaturated radical (C=C) in the epoxy compound per 1 mol Si-bonded hydrogen in the hydrogen siloxane, and the olefinic unsaturated polyether is used in an amount of from 0 to 0.2 mol, of the olefinic unsaturated radical (C=C) in the polyether per 1 mol Si-bonded hydrogen in the hydrogen siloxane, (ii) reacting, in a second step
the resulting epoxy functional siloxane obtained from the first step with a polyetheramine of the formula $$NZ_2R^3(OR^2)_fNZ^1_2 \qquad (VII)$$

with the proviso that the polyetheramine is used in an amount of equal to or greater than 1.2 mols amino groups in the polyetheramine per 1 mol epoxy groups in the epoxy functional siloxane, and obtaining an amino-organopolysiloxane.

7. The process of claim 6, further comprising reacting the olefinic unsaturated epoxy compound and the olefinic unsaturated polyether stepwise with the hydrogen siloxane.

8. The process of claim 6, wherein $R^2$ and $R^3$ are, each independently, $C_2$ or $C_3$ alkylene radicals.

9. The process of claim 6, wherein the polyetheramine is a primary polyetherdiamine, wherein Z and $Z^1$ are hydrogen.

10. A composition comprising an amino-organopolysiloxane prepared by the process of claim 6.

11. An aqueous composition comprising an amino-organopolysiloxane prepared by the process of claim 6.

12. A process for preparing an amino-organopolysiloxane of claim 1, comprising:

(i) reacting in a first step
a hydrogen siloxane of the formula $$HR^*_2SiO(R_2SiO)_uSiR^*_2H \qquad (IV),$$

wherein u is an integer from 1 to 500, with an olefinic unsaturated epoxy compound of the formula $$CH_2=CH-(CH_2)_w-O-R^5-CH(O)CH_2 \qquad (V),$$

and an olefinic unsaturated polyether of the formula $$CH_2=CH-R^9-(OR^2)_gOH \qquad (VI),$$

wherein $R^9$ is $C_1$ to $C_4$ alkylene radical,
in the presence of a catalyst comprising platinum or its compounds or complexes,
to form an epoxy functional siloxane;
with the proviso that the olefinic unsaturated epoxy compound is used in an amount of from 0.8 to 1 mol, of the olefinic unsaturated radical (C=C) in the epoxy compound per 1 mol Si-bonded hydrogen in the hydrogen siloxane, and the olefinic unsaturated polyether is used in an amount of from 0 to 0.2 mol, of the olefinic unsaturated radical (C=C) in the polyether per 1 mol Si-bonded hydrogen in the hydrogen siloxane, (ii) reacting, in a second step
the resulting epoxy functional siloxane obtained from the first step with a polyetheramine of the formula $$NZ_2R^3(OR^2)_jNZ^1_2 \qquad (VII)$$

with the proviso that the polyetheramine is used in an amount of equal to or greater than 1.2 mols amino groups in the polyetheramine per 1 mol epoxy groups in the epoxy functional siloxane,
and obtaining an amino-organopolysiloxane.

13. A composition comprising an amino-organopolysiloxane of claim 1.

14. An aqueous composition comprising an amino-organopolysiloxane of claim 1.

15. An aqueous composition of claim 14, wherein the composition is an aqueous emulsion.

16. In a process for treating organic fibers with an aqueous composition, the improvement comprising treating with an amino-organopolysiloxane of claim 1.

17. The process for treating organic fibers of claim 16, wherein the aqueous composition is an aqueous emulsion.

18. The process for treating organic fibers of claim 16, wherein the hydrophilicity and softness of the organic fibers is improved relative to untreated organic fibers.

19. The process of claim 16, wherein the organic fiber is in the form of a textile fabric.

\* \* \* \* \*